United States Patent [19]

Franke et al.

[11] Patent Number: 4,563,474

[45] Date of Patent: Jan. 7, 1986

[54] PHTHALIMIDES AND THIENOPYRROLS AS DRUGS

[75] Inventors: Albrecht Franke, Wachenheim; Gerd Steiner, Kirchheim; Hans-Peter Hofmann, Limburgerhof; Claus-Dieter Müller, Viernheim; Hans-Jürgen Teschendorf, Dudenhofen, all of Fed. Rep. of Germany

[73] Assignee: BASF Aktiengesellschaft, Ludwigshafen, Fed. Rep. of Germany

[21] Appl. No.: 552,443

[22] Filed: Nov. 16, 1983

[30] Foreign Application Priority Data

Nov. 18, 1982 [DE] Fed. Rep. of Germany ....... 3242477

[51] Int. Cl.<sup>4</sup> ................ C07D 209/48; C07D 275/02; C07D 275/04; A61K 31/40
[52] U.S. Cl. .................... 514/417; 548/477; 548/453; 548/153; 514/414; 514/373
[58] Field of Search ............... 548/477, 453; 424/274; 514/417, 414

[56] References Cited

U.S. PATENT DOCUMENTS

| | | | |
|---|---|---|---|
| 2,492,554 | 7/1946 | Chodroff | 548/477 |
| 2,992,223 | 7/1961 | Frazza | 548/477 |
| 3,980,634 | 9/1976 | Weaver | 548/477 |
| 4,115,398 | 9/1978 | Nakamura et al. | 548/454 |
| 4,325,963 | 4/1982 | Hitzel et al. | 514/421 |

FOREIGN PATENT DOCUMENTS

| | | | |
|---|---|---|---|
| 454944 | 3/1949 | Canada | 548/477 |
| 629816 | 8/1949 | United Kingdom | 548/477 |
| 2087388 | 5/1982 | United Kingdom . | |

OTHER PUBLICATIONS

"Beilsteins Handbuch der Organischen Chemie", vol. 21, II, pp. 358–359.
Arzneim. Forschung, Drug Res. 32, No. 9, 1982, Becker et al., The Metabolic Fate of Supidimide in the Rat.
Butskus, P. F., "Cyanoethylation . . ." Russian Chem. Rev. 30, No. 11, (1961), pp. 583–594.

*Primary Examiner*—Donald G. Daus
*Assistant Examiner*—G. Hendricks
*Attorney, Agent, or Firm*—Oblon, Fisher, Spivak, McClelland & Maier

[57] ABSTRACT

Heterocyclically substituted nitriles of the formula I

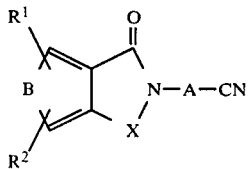

where X is $SO_2$, CO, S, SO or $CH_2$, A is an alkylene or alkenylene radical of not more than 6 carbon atoms, B is —CH=CH— or S, and $R^1$ and $R^2$ are each hydrogen, halogen, $C_1$–$C_3$-alkyl, $C_1$–$C_3$-alkoxy, nitro or trifluoromethyl, and their preparation and use.

The novel substances are useful for treating disorders.

17 Claims, No Drawings

PHTHALIMIDES AND THIENOPYRROLS AS DRUGS

The present invention relates to heterocyclically substituted nitriles, processes for their preparation and therapeutic compositions containing these compounds and the use of these compositions in treating disorders.

It has been disclosed that the active compound supidimide (3-(2,3-dihydro-1,1-dioxido-3-oxo-1,2-benzisothiazol-2-yl)-2-oxopiperidine; Arzneim. Forsch. 32 (1982), 1101) has useful properties as a tranquilizer and hypnotic.

We have found that heterocyclically substituted nitriles of the formula I

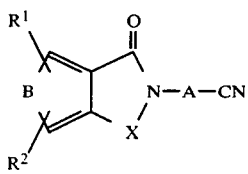   I where X is $SO_2$, CO, S, SO or $CH_2$, A is an alkylene or alkenylene radical of not more than 6 carbon atoms, B is —CH=CH— or S and $R^1$ and $R^2$ are each hydrogen, halogen, $C_1$–$C_3$-alkyl, $C_1$–$C_3$-alkoxy, nitro or trifluoromethy possess useful pharmacological properties.

X is preferably $SO_2$ or CO, A is preferably 2-methylbutan-2-ylene or, in particular, 2-methylpropen-2-ylene (in these cases, A—CN is $CH_2$—$CH_2$—$C(CH_3)$=CH—CN or $CH_2$—$C(CH_3)$=CH—CN), B is preferably —CH=CH—, and $R^1$ and $R^2$ are each preferably hydrogen, chlorine or fluorine.

It should be pointed out that the novel compounds can occur as cis and trans isomers if A is alkenylene.

The compounds below are particularly active: 3-(2,3-dihydro-1,1-dioxide-3-oxo-1,2-benzisothiazol-2-yl)-1-cyano-2-methylprop-1-ene, 3-(2,3-dihydro-1,1-dioxido-3-oxo-4-chloro-1,2-benzisothiazol-2-yl)-1-cyano-2-methylprop-1-ene, 3-(2,3-dihydro-1,1-dioxido-3-oxo-5-fluoro-1,2-benzisothiazol-2-yl)-1-cyano-2-methylprop-1-ene, 3-(2,3-dihydro-1,1-dioxido-3-oxo-5-chloro-1,2-benzisothiazol-2-yl)-1-cyano-2-methylprop-1-ene, 4-(2,3-dihydro-1,1-dioxido-3-oxo-1,2-benzisothiazol-2-yl)-1-cyano-2-methylbut-1-ene and 4-phthalimido-2-yl-1-cyano-2-methylbut-1-ene.

The novel compounds can be prepared by a process in which (a) a compound of the formula II

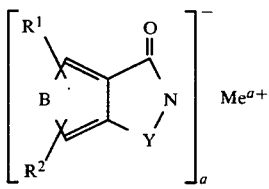   II where Y has the same meaning as X, with the exception of SO, Me is an alkali metal or alkaline earth metal having a valency a, and B, $R^1$ and $R^2$ have the above meanings, is reacted with a compound of the formula III Hal—A—CN   III where A has the above meanings and Hal is halogen, or (b) where Alk is a straight-chain or methyl-branched alkylene or alkenylene radical, a compound of the formula IV

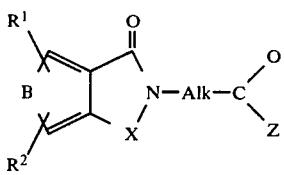   IV where X, B, $R^1$ and $R^2$ have the above meanings, Alk is alkyl of 1 to 3 carbon atoms and Z is hydrogen or methyl, is reacted with a phosphonate of the formula V

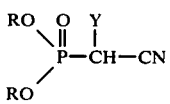   V where R is alkyl of 1 to 3 carbon atoms and Y is hydrogen or methyl, and, if desired, any sulfur atom present in the resulting compound is oxidized or any C=C double bond present in the side chain is hydrogenated.

The alkali metal or alkaline earth metal salts used for process (a) are obtained from the free bases using a strong alkali metal or alkaline earth metal base, such as the hydroxide, alcoholate or hydride, or an appropriate organometallic compound, but preferably using sodium hydride, in an inert organic solvent, such as a cyclic saturated ether, in particular tetrahydrofuran or dioxane, or in a polar aprotic solvent, preferably dimethylformamide.

The reaction of the resulting salt with a compound of the formula III is advantageously carried out at from 0° to 150° C., and is generally complete within from 3 to 10 hours. Suitable solvents are the inert organic ones mentioned above, preferably dimethylformamide.

Reaction (b) is carried out under the conditions of a Wittig-Horner reaction, in an inert solvent in the presence of one molar equivalent of a base, preferably sodium alcoholate, sodium hydride or sodium amide, at from 20° to 80° C.

Examples of suitable inert solvents are lower alcohols, eg. methanol, ethanol or propanol, or ethers, eg. diethyl ether, tetrahydrofuran or dioxane, or polar aprotic solvents, eg. dimethylformamide. The latter is preferred.

The compounds of the formula I in which X is sulfur can be converted to the corresponding SO or $SO_2$ compounds by oxidation. Oxidation to the SO compound can be carried out, for example, by adding 3-chloroperoxybenzoic acid in an inert organic solvent, such as a halohydrocarbon or an ether.

Hydrogenation of a double bond in the side chain is most advantageously carried out catalytically with hydrogen, suitable catalysts being noble metals, such as palladium on carbon, or platinum.

The reaction can be carried out at room temperature and under atmospheric pressure. Suitable solvents are lower alcohols, eg. methanol or ethanol, cyclic saturated ethers, eg. tetrahydrofuran or dioxane, esters, eg.

ethyl acetate, or dipolar aprotic amides, eg. dimethylformamide.

The majority of the compounds of the formula I are obtained in the form of crystals, and can be purified by recrystallization from a conventional organic solvent, preferably from a lower alcohol, such as ethanol, or a lower ester, preferably ethyl acetate, or by column chromatography.

The compounds according to the invention have useful pharmacological properties. They are useful, for example, for the treatment of psychological disturbances, in particular depression, and as sedatives and tranquilizers.

To analyze the pharmacological properties, the following actions were tested:

Sedative action

The test substances were administered orally to groups comprising three female NMRI mice each. The orientation hypermotility induced by a new environment is determined photoelectrically, 30 minutes after administration of the substance, over a period of 30 minutes.

The $ED_{50}$, ie. the dose which produces 50% reduction in orientation hypermotility compared to untreated control animals, was determined.

Antidepressant action

In male mice (Swiss, weight 20–26 g), reserpine (2.15 mg/kg, administered subcutaneously) causes a decrease in body temperature by 3° C. on average, measured 2 hours after administration of reserpine at an ambient temperature of 20°–22° C. Antidepressants produce a dose-dependent inhibition of this hypothermia. The test substances were administered orally 60 minutes before reserpine.

The $ED_{50}$, ie. the dose which inhibits the reserpine-induced hypothermia by 50%, was determined from the linear regression between log dose (mg/kg) and the relative decrease in hypothermia.

Supidimide is known to have a weak suppressant effect on the central nervous system, and this effect was also found in our test for sedative action. With regard to the sedative action (cf. Table), the novel substances prove to be 10 times as active as supidimide.

Moreover, the novel compounds surprisingly have an antidepressant action, which is completely absent in the case of supidimide up to the maximum test dose of 2,150 mg/kg (administered orally). In contrast, the novel substances are effective even in low doses (cf. Table), and are substantially more active than the standard antidepressant imipramine.

Compared with the sedative action, the anti-depressant action of the novel substances is detectable at a substantially lower dose (by as much as about 90 times). The antidepressant effect of the novel compounds clearly dominates the action spectrum.

TABLE

| Substance of Example No. | Antidepressant action (mouse) $ED_{50}$ (mg/kg, administered orally) | Sedative action (mouse) $ED_{50}$ (mg/kg, administered orally) |
| --- | --- | --- |
| 1 + 2 | 3.5 | 50 |
| 4 | 3.1 | 52 |
| 6 | 1.1 | 100 |
| 11 | 18.9 | 68 |
| 12 | 11.4 | 49 |
| 18 | 4.5 | 29 |
| Supidimide | 2,150 | 277 |
| Imipramine | 6.8 | about 100 |

The present invention therefore furthermore relates to drugs which contain a compound of the formula I, and to the use of the novel compounds in the treatment of disorders.

The novel compounds may be employed in the conventional solid or liquid pharmaceutical forms, such as tablets, film tablets, capsules, powders, granules, coated tablets, suppositories or solutions. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents and/or antioxidants (cf. H. Sucker et al.: Pharmazeutische Technologie, Thieme-Verlag, Stuttgart, 1978). The resulting forms for administration normally contain from 0.1 to 99% by weight of the active compound.

The dosage of the compounds according to the invention depends the age, condition and weight of the patient and on the route of administration. For example, in the case of oral administration, the daily dose of active compound is, as a rule, from 5 to 300 mg.

The Examples which follow illustrate the invention.

EXAMPLE 1

(a) Preparation of the starting material 20.0 g (250 millimoles) of dimethylacrylonitrile were dissolved in 200 ml of carbon tetrachloride, and 49.0 g (282 millimoles) of N-bromosuccinimide were added a little at a time, while stirring thoroughly.

A pinch of azobisisobutyronitrile was added, after which the reaction mixture was slowly heated to 80° C. After 4 hours, it was allowed to cool, and the precipitated succinimide was filtered off under suction. The filtrate was evaporated to dryness. 39.7 g (99%) of 3-bromo-2-methyl-3-cyanoprop-1-ene were isolated as a brownish oil, which was sufficiently pure for further reaction.

(b) Preparation of the end product 41.3 g (258 millimoles) of 3-bromo-2-methyl-3-cyanoprop-1-ene were slowly added dropwise to a thoroughly stirred solution of 32.8 g (164 millimoles) of sodium saccharin in 300 ml of dimethylformamide (slightly exothermic reaction). The reaction mixture was then stirred for 5 hours at 80° C., after which it was cooled and poured onto 3 liters of ice-water. The precipitate was filtered off under suction and washed thoroughly with water. 40.3 g of pale crystals were isolated, and these were recrystallized from 340 ml of ethanol with the addition of active carbon. 30.2 g (70%) of 3-(2,3-dihydro-1,1-dioxido-3-oxo-1,2-benzisothiazol-2-yl)-1-cyano-2-methylprop-1-ene of melting point 119°–121° C. were obtained. The $^1$H-NMR spectrum showed that the cis/trans isomer ratio was 2:1.

EXAMPLE 2

(a) Preparation of the starting material 26 ml (324 millimoles) of chloroacetone were slowly added dropwise to 40.0 g (200 millimoles) of sodium saccharin, while stirring (exothermic reaction). The temperature was gradually increased to 110° C., and the reaction mixture was stirred at this temperature for 5 hours, after which it was cooled. An excess of ice-water was added, and stirring was continued for a further hour. The precipitated solid was filtered off under suction, recrystallized from ethanol and dried in a drying oven under reduced pressure at 50° C. to give 35.2 g (74%) of N-acetonylsaccharin of melting point 142°–143° C.

(b) Preparation of the end product 7.4 g (42 millimoles) of diethylcyanomethyl phosphonate and 6.8 g (38 millimoles) of 30% strength sodium methylate were simultaneously added dropwise to 10.0 g (42 millimoles) of N-acetonylsaccharin in 200 ml of dimethylformamide, while stirring thoroughly, the temperature increasing to 34° C. The reaction mixture was stirred for a further hour at room temperature, after which the contents of the flask were poured onto ice-water and extracted three times with methylene chloride, the organic phase was dried and evaporated down under reduced pressure, and the crude product was recrystallized from ethanol to give 2.5 g (23%) of 3-(2,3-dihydro-1,1-dioxido-3-oxo-1,2-benzisothiazol-2-yl)-1-cyano-2-methylprop-1-ene of melting point 118°–121° C.

EXAMPLE 3

10.0 g (66 millimoles) of 2,3-dihydro-3-oxo-1,2-benzisothiazole were suspended in 140 ml of dimethylformamide, and 2.0 g (66 millimoles) of 80% strength sodium hydride were added a little at a time, while stirring thoroughly. After 15 minutes, 12.8 g (80 millimoles) of 3-bromo-2-methyl-3-cyanoprop-1-ene were slowly added dropwise, and the reaction mixture was stirred for 2 hours at 80° C. and then cooled. The solvent was distilled off under reduced pressure, the mixture was taken up in ice-water and extracted with methylene chloride, and the organic phase was washed thoroughly with $H_2O$, dried and evaporated down. The crude product (16 g of a dark oil) was then purified by column chromatography (silica gel, mobile phase 95:5 mixture of methylene chloride and methanol). 3.5 g (23%) of 3-(2,3-dihydro-3-oxo-1,2-benzisothiazol-2-yl)-1-cyano-2-methylprop-1-ene of melting point 128°–130° C. were obtained.

The following compounds were prepared by a method similar to that described in Example 3:

4. 3-(2,3-Dihydro-4-chloro-1,1-dioxido-3-oxo-1,2-benzisothiazol-2-yl)-1-cyano-2-methylprop-1-ene, mp. 127°–128° C.
5. 3-(2,3-Dihydro-5-fluoro-1,1-dioxido-3-oxo-1,2-benzisothiazol-2-yl)-1-cyano-2-methylprop-1-ene, mp. 125°–127° C.
6. 3-(2,3-Dihydro-5-chloro-1,1-dioxido-3-oxo-1,2-benzisothiazol-2-yl)-1-cyano-2-methylprop-1-ene, mp. 120°–122° C.
7. 3-(2,3-Dihydro-4-methoxy-1,1-dioxido-3-oxo-1,2-benzisothiazol-2-yl)-1-cyano-2-methylprop-1-ene, mp. 108°–110° C.
8. 3-(2,3-Dihydro-4-methoxy-7-nitro-1,1-dioxido-3-oxo-1,2-benzisothiazol-2-yl)-1-cyano-2-methylprop-1-ene, mp. 72°–73° C.
9. 3-(2,3-Dihydro-4-chloro-7-nitro-1,1-dioxido-3-oxo-1,2-benzisothiazol-2-yl)-1-cyano-2-methylprop-1-ene, mp. 80°–82° C.
10. 3-(2,3-Dihydro-4-chloro-5-bromo-1,1-dioxido-3-oxo-1,2-benzisothiazol-2-yl)-1-cyano-2-methylprop-1-ene, mp. 195°–196° C.
11. 3-(Phthalimid-2-yl)-1-cyano-2-methylprop-1-ene, mp. 139°–140° C.
12. 3-(Phthalimidin-2-yl)-1-cyano-2-methylprop-1-ene, mp. 142°–144° C.
13. 3-(2,3-Dihydro-1,1-dioxido-3-oxo-1,2-thieno[3,4-d]isothiazol-2-yl)-1-cyano-2-methylprop-1-ene, mp. 153°–154° C.

EXAMPLE 14

18.2 g (150 millimoles) of 2-cyano-4-chlorobut-2-ene were slowly added dropwise to 20.0 g (100 millimoles) of sodium saccharin in 100 ml of absolute dimethylformamide, while stirring thoroughly. The reaction mixture was stirred for a further 4 hours at 40° C., after which the precipitated sodium chloride was filtered off and the filtrate was evaporated down under reduced pressure to about 30 ml. After 400 ml of water had been added, the oil initially formed slowly crystallized. The crystals were filtered off under suction, recrystallized from ethanol and dried in a drying oven under reduced pressure at 50° C. to give 17.4 g (66%) of 4-(2,3-dihydro-1,1-dioxido-3-oxo-1,2-benzisothiazol-2-yl)-2-cyanobut-2-ene of melting point 107°–108° C.

The following compounds were obtained by a method similar to that described in Example 14:

15. 4-(2,3-Dihydro-1,1-dioxido-3-oxo-1,2-thieno[3,4-d]isothiazol-2-yl)-2-cyanobut-2-ene, mp. 154°–155° C.
16. 4-(Phthalimid-2-yl)-2-cyanobut-2-ene, mp. 101°–102° C.

EXAMPLE 17

(a) Preparation of the starting material 9.0 g (76 millimoles) of 4-chlorobutan-2-one were slowly added dropwise to 10.0 g (50 millimoles) of sodium saccharin in 100 ml of absolute dimethylformamide, while stirring. The temperature was then gradually increased to 80° C., and the reaction mixture was stirred at this temperature for 5 hours, after which it was cooled. An excess of ice-water was added, and stirring was continued for a further hour. The precipitated solid was filtered off under suction, recrystallized from ethanol and dried in a drying oven under reduced pressure at 50° C. to give 10.9 g (86%) of N-(2-oxobut-4-yl)-saccharin of melting point 118°–119° C.

(b) Preparation of the end product 9.5 g (54 millimoles) of diethyl cyanomethyl phosphonate and 8.7 g (48 millimoles) of 30% strength sodium methylate were simultaneously added dropwise to 10.0 g (40 millimoles) of N-(2-oxobut-4-yl)-saccharin in 150 ml of absolute dimethylformamide, while stirring thoroughly. The reaction mixture was stirred for a further 5 hours at 40° C., after which the contents of the flask were poured onto ice-water, and the precipitated crystals were filtered off under suction and recrystallized from ethanol to give 2.2 g (20%) of 4-(2,3-dihydro-1,1-dioxido-3-oxo-1,2-benzisothiazol-2-yl)-1-cyano-2-methylbut-1-ene of melting point 117°–118° C.

The following compounds were prepared by a similar method:
18. 4-(Phthalimid-2-yl)-1-cyano-2-methylbut-1-ene, mp. 130°–131° C.

EXAMPLE 19

10.0 g (38 millimoles) of 3-(2,3-dihydro-1,1-dioxido-3-oxo-1,2-benzisothiazol-2-yl)-1-cyano-2-methylprop-1-ene (Example 1) were dissolved in 200 ml of ethanol and 100 ml of dimethylformamide, 1 g of palladium on active carbon (10%) was added and hydrogenation was carried out for 12 hours at room temperature and under atmospheric pressure. The mixture was filtered, the filtrate was evaporated down under reduced pressure and the resulting greenish oil was purified by column chromatography (silica gel, mobile phase 85:15 mixture of toluene and methanol) to give 4.8 g (48%) of 3-(2,3-dihydro-1,1-dioxido-3-oxo-1,2-benzisothiazol-2-yl)-1-cyano-2-methylpropane in the form of an oil which slowly crystallized through. Mp 83°–84° C.

The following compounds were prepared by a similar method:
20. 2-(2,3-Dihydro-1,1-dioxido-3-oxo-1,2-benzisothiazol-2-yl)-1-cyanoethane, mp. 146°–147° C.
21. 3-(2,3-Dihydro-1,1-dioxido-3-oxo-1,2-benzisothiazol-2-yl)-1-cyanopropane, mp. 97°–98° C.
22. 4-(2,3-Dihydro-1,1-dioxido-3-oxo-1,2-benzisothiazol-2-yl)-1-cyanobutane, mp. 107°–108° C.
23. 3-(2,3-Dihydro-1,1-dioxido-3-oxo-1,2-thieno[3,4-d]isothiazol-2-yl)-1-cyanopropane, mp. 95°–96° C.
24. 4-(2,3-Dihydro-1,1-dioxido-3-oxo-1,2-thieno[3,4-d]isothiazol-2-yl)-1-cyanobutane, mp. 120°–121° C.

EXAMPLE 25

5.8 g (26 millimoles) of 3-(2,3-dihydro-3-oxo-1,2-benzisothiazol-2-yl)-1-cyano-2-methylprop-1-ene (Example 3) were dissolved in 160 ml of methylene chloride, and 5.4 g (26 millimoles) of 85% strength 3-chloroperoxybenzoic acid were added, while stirring thoroughly. The mixture was stirred for a further 3–4 hours, and was then evaporated down to about 40 ml. The colorless crystals of 3-chlorobenzoic acid which were precipitated were filtered off under suction, the filtrate was evaporated down and the residue was purified by column chromatography (silica gel, toluene/methanol) to give 3.4 g (53%) of 3-(2,3-dihydro-1-oxido-3-oxo-1,2-benzisothiazol-2-yl)-1-cyano-2-methylprop-1-ene of melting point 91°–93° C.

The following compounds can be prepared by methods similar to those described in Examples 1, 2, 3, 14, 17, 19 or 25:
26. 3-(2,3-Dihydro-1,1-dioxido-3-oxo-6-chloro-1,2-benzisothiazol-2-yl)-1-cyano-2-methylprop-1-ene.
27. 3-(2,3-Dihydro-1,1-dioxido-3-oxo-7-chloro-1,2-benzisothiazol-2-yl)-1-cyano-2-methylprop-1-ene.
28. 3-(2,3-Dihydro-1,1-dioxido-3-oxo-4-trifluoromethyl-1,2-benzisothiazol-2-yl)-1-cyano-2-methylprop-1-ene.
29. 3-(2,3-Dihydro-1,1-dioxido-3-oxo-5-trifluoromethyl-1,2-benzisothiazol-2-yl)-1-cyano-2-methylprop-1-ene.
30. 3-(2,3-Dihydro-1,1-dioxido-3-oxo-4-methyl-1,2-benzisothiazol-2-yl)-1-cyano-2-methylprop-1-ene.
31. 3-(2,3-Dihydro-1,1-dioxido-3-oxo-5-propyl-1,2-benzisothiazol-2-yl)-1-cyano-2-methylprop-1-ene.
32. 3-(2,3-Dihydro-1,1-dioxido-3-oxo-1,2-benzisothiazol-2-yl)-1-cyano-2-ethylprop-1-ene.
33. 3-(2,3-Dihydro-1,1-dioxido-3-oxo-1,2-benzisothiazol-2-yl)-1-cyano-2,3-dimethylprop-1-ene.
34. 4-(4-Chlorophthalimid-2-yl)-1-cyano-2-methylbut-1-ene.
35. 4-(5-Chlorophthalimid-2-yl)-1-cyano-2-methylbut-1-ene.

We claim:
1. A method of treating a psychological disturbance in a patient suffering therefrom, which comprises administering an effective amount of a heterocyclically substituted nitrile of the formula I

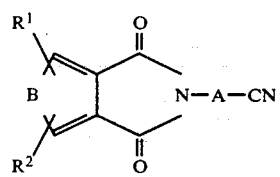

where A is an alkylene or an alkenylene radical of not more than 6 carbon atoms, B is —CH=CH— or S, and $R^1$ and $R^2$ are each independently at least one member selected from the group consisting of hydrogen, halogen, $C_1$-$C_3$-alkyl, $C_1$-$C_3$-alkoxy, nitro and trifluoromethyl; said physchological disturbance consisting of any of the following: a psychological disturbance requiring a sedative, a tranquilizer or an antidepressant.

2. The method of claim 1, wherein said psychological disturbance is depression.

3. A method of sedating a patient, said method comprising administering, to said patient, an effective amount of a heterocyclically substituted nitrile of the formula I

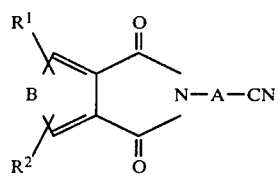

where A is an alkylene or an alkenylene radical of not more than 6 carbon atoms, B is —CH=CH— or S, and $R^1$ and $R^2$ are each independently at least one member selected from the group consisting of hydrogen, halogen, $C_1$-$C_3$-alkyl, $C_1$-$C_3$ alkoxy, nitro and trifluoromethyl.

4. A method of treating reserpine induced hypothermia, said method comprising administering a heterocyclically substituted nitrile of the formula I

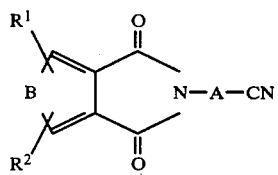

where A is an alkylene or an alkenylene radical of not more than 6 carbon atoms, B is —CH=CH— or S, and $R^1$ and $R^2$ are each independently at least one member selected from the group consisting of hydrogen, halogen, $C_1$–$C_3$-alkyl, $C_1$–$C_3$ alkoxy, nitro and trifluoromethyl.

5. A method of treating psychologically induced hypermotility, said method comprising administering a heterocyclically substituted nitrile of the formula I

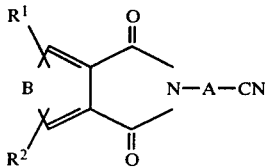

where A is an alkylene or an alkenylene radical of not more than 6 carbon atoms, B is —CH=CH— or S, and $R^1$ and $R^2$ are each independently at least one member selected from the group consisting of hydrogen, halogen, $C_1$–$C_3$-alkyl, $C_1$–$C_3$ alkoxy, nitro and trifluoromethyl.

6. A method of treating orientation hypermotility, said method comprising administering a heterocyclically substituted nitrile of the formula I

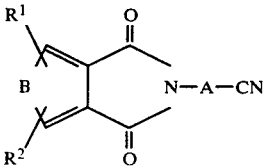

where A is an alkylene or an alkenylene radical of not more than 6 carbon atoms, B is —CH=CH— or S, and $R^1$ and $R^2$ are each independently at least one member selected from the group consisting of hydrogen, halogen, $C_1$–$C_3$-alkyl, $C_1$–$C_3$ alkoxy, nitro and trifluoromethyl.

7. The method of claim 1, wherein A is 2-methylbutan-2-ylene.

8. The method of claim 1, wherein A is 2-methylpropen-2-ylene.

9. The method of claim 1, wherein B is —CH=CH—.

10. The method of claim 1, wherein $R^1$ and $R^2$ each independently comprise H, Cl or F.

11. The method of claim 1, wherein the nitrile comprises 4-phthalimido-2-yl-1-cyano-2-methylbut-1-ene.

12. The method of claim 1, wherein the nitrile comprises 3-(phthalimid-2-yl)-1-cyano-2-2-methylprop-1-ene.

13. The method of claim 1, wherein the nitrile comprises 3-(phthalimidin-2-yl)-1-cyano-2-methylprop-1-ene.

14. The method of claim 1, wherein the nitrile comprises 4-(4-chlorophthalimid-2-yl)-1-cyano-2-methylbut-1-ene.

15. The method of claim 1, wherein the nitrile comprises 4-(5-chlorophthalimid-2-yl)-1-cyano-2-methylbut-1-ene.

16. The method of claim 1, wherein said nitrile is administered in a solid or liquid pharmaceutical form containing from 0.1 to 99% by weight of the nitrile.

17. The method of claim 1, wherein from 5 to 300 mg of said nitrile is administered orally to the patient daily.

* * * * *